(12) United States Patent
Whitsett, Jr. et al.

(10) Patent No.: US 12,263,170 B2
(45) Date of Patent: *Apr. 1, 2025

(54) SYSTEMS AND METHODS FOR TREATING CANCER

(71) Applicants: Dignity Health, Phoenix, AZ (US); The Translational Genomics Research Institute, Phoenix, AZ (US)

(72) Inventors: Timothy G. Whitsett, Jr., Phoenix, AZ (US); Landon J. Inge, Phoenix, AZ (US)

(73) Assignees: Dignity Health, San Francisco, CA (US); The Translational Genomics Research Institute, Phoenix, AZ (US)

( * ) Notice: Subject to any disclaimer, the term of this patent is extended or adjusted under 35 U.S.C. 154(b) by 899 days.

This patent is subject to a terminal disclaimer.

(21) Appl. No.: 17/220,977

(22) Filed: Apr. 2, 2021

(65) Prior Publication Data

US 2021/0251998 A1 Aug. 19, 2021

Related U.S. Application Data

(63) Continuation of application No. 16/565,605, filed on Sep. 10, 2019, now Pat. No. 10,993,946, which is a (Continued)

(51) Int. Cl.
*A61K 31/519* (2006.01)
*A61K 31/282* (2006.01)
(Continued)

(52) U.S. Cl.
CPC .......... *A61K 31/519* (2013.01); *A61K 31/282* (2013.01); *A61K 31/7068* (2013.01);
(Continued)

(58) Field of Classification Search
CPC ................ A61K 31/519; A61K 31/282; A61K 31/7068; A61K 33/24; A61K 33/243; A61K 45/06; A61K 2300/00; A61P 35/00
See application file for complete search history.

(56) References Cited

U.S. PATENT DOCUMENTS 10,449,197 B2 * 10/2019 Whitsett, Jr. ...... A61K 31/7068
10,993,946 B2 * 5/2021 Whitsett, Jr. ...... A61K 31/7068
(Continued)

FOREIGN PATENT DOCUMENTS

WO 2015138834 A1 9/2015

OTHER PUBLICATIONS

Schrag D et al. American Society of Clinical Oncology Technology Assessment: chemotherapy sensitivity and resistance assays. J Clin Oncol. Sep. 1, 2004;22(17):3631-8. doi: 10.1200/JCO.2004.05.065. Epub Aug. 2, 2004. PMID: 15289488. (Year: 2004).*

(Continued)

*Primary Examiner* — Bruck Kifle
*Assistant Examiner* — Kevin S Martin
(74) *Attorney, Agent, or Firm* — Polsinelli PC

(57) ABSTRACT

Embodiments of the invention provide a method of treating cancer, the method comprising providing a subject having cancer cells, and contacting the cancer cells with a therapeutically effective amount of a G2/M checkpoint inhibitor. Embodiments of the invention also provide a method of treating cancer in a subject, the method comprising the steps of: (a) receiving a sample of the cancer cells from the subject; (b) determining if at least a portion of the sample of the cancer cells is LKB1 deficient; and (c) contacting the cancer cells with a therapeutically effective amount of a G2/M checkpoint inhibitor. Embodiments of the invention also provide a method of treating cancer in a subject, the method comprising contacting the cancer cells with a thera-
(Continued)

peutically effective amount of a Wee1 inhibitor and a therapeutically effective amount of a second pharmaceutical composition. Embodiments of the invention also provide a method of prognosing or determining the severity of cancer in a subject comprising (a) determining the presence or absence of LKB1 in the cancer cells of the subject; and (b) prognosing the severity of cancer based on the presence of LKB1 deficiency in the cancer cells of the subject.

18 Claims, 9 Drawing Sheets

Related U.S. Application Data continuation of application No. 15/740,546, filed as application No. PCT/US2015/062785 on Nov. 25, 2015, now Pat. No. 10,449,197.

(60) Provisional application No. 62/187,442, filed on Jul. 1, 2015.

(51) Int. Cl.
| | | |
|---|---|---|
| *A61K 31/7068* | (2006.01) | |
| *A61K 33/24* | (2019.01) | |
| *A61K 33/243* | (2019.01) | |
| *A61K 45/06* | (2006.01) | |
| *A61P 35/00* | (2006.01) | |

(52) U.S. Cl.
CPC ............ *A61K 33/24* (2013.01); *A61K 33/243* (2019.01); *A61K 45/06* (2013.01); *A61P 35/00* (2018.01); *A61K 2300/00* (2013.01)

(56) References Cited

U.S. PATENT DOCUMENTS

| | | |
|---|---|---|
| 2013/0231301 A1 | 9/2013 | Davies et al. |
| 2013/0338040 A1 | 12/2013 | Hayes et al. |
| 2014/0343071 A1* | 11/2014 | Shumway .............. A61K 45/06 514/259.3 |

OTHER PUBLICATIONS

Kadara H, Kabbout M, Wistuba II. Pulmonary adenocarcinoma: a renewed entity in 2011. Respirology. Jan. 2012; 17(1):50-65. doi: 10.1111/j.1440-1843.2011.02095.x. PMID: 22040022; PMCID: PMC3911779. (Year: 2012).*
Bridges et al. in Clinical Cancer Research 17(17) 5638-5648 (2011) (Year: 2011).
Ji et al. in Nature 448(16) 807-810 (2007) (Year: 2007).
Barlesi et al. in Annals of Oncology 22:2466-2470 (2011) (Year: 2011).
National Cancer Institute, Adenocarcinoma Definition (https://www.cancer.gov/publications/dictionaries/ cancer-terms/def/adenocarcinoma), (retrieved from the internet Oct. 14, 2020.
Gelderblom, H et al. "he drawbacks and advantages of vehicle selection for drug formulation" European Journal of Cancer 37, 2001, 1590-1598.
Patent Cooperation Treaty, International Search Report and Written Opinion, International Application No. PCT/US2015/062785, date of mailing Feb. 4, 2016, 4 pages.
Inge et al. "LKB1 inactivation sensitizes non-small cell lung cancer to pharmac:ologir.r11 aggravation of ER stress," Cancer Letters, Jul. 7, 2014 {Jul. 14, 2014), vol. 352, Iss. 2, pp. 187-195.

* cited by examiner

A549

H2030

SYSTEMS AND METHODS FOR TREATING CANCER

CROSS REFERENCE TO RELATED APPLICATIONS

This application is a continuation U.S. patent application Ser. No. 16/565,605, filed Sep. 10, 2019, currently pending, which is a continuation of U.S. Pat. No. 10,449,197, filed Dec. 28, 2017, which is a National Phase of International Application No. PCT/US2015/062785, filed Nov. 25, 2015, now expired, which claimed priority under 35 U.S.C. § 119 (e) to U.S. Provisional Patent Application No. 62/187,442, filed Jul. 1, 2015, now expired, the contents of which are herein incorporated by reference in their entirety.

FIELD OF THE INVENTION

The present invention is generally related to systems and methods for treating one or more forms of cancer, and particularly related to systems and methods for treating non-small cell lung cancer, including particular forms of non-small cell lung cancer, including LKB1 deficient forms of non-small cell lung cancer.

BACKGROUND OF THE INVENTION

Lung cancer remains the leading cause of cancer mortality in the US and throughout the world, (Jemal A, et al. Global cancer statistics. CA Cancer J Clin 61 (2): 69-90 (2011), with most patients presenting with advanced stage disease. The five-year survival rate for advanced stage non-small cell lung cancer (NSCLC) remains below 10%, necessitating the need for novel therapeutic strategies against advanced disease. A significant clinical hurdle to reduce mortality in NSCLC is the propensity for tumor cell invasiveness and metastasis. Despite pharmacological advances for NSCLC, current treatments have limited efficacy in metastatic disease, and the majority of patients succumb to the overwhelming tumor burden resulting from tumor spread. Even molecularly targeted therapeutics such as the epidermal growth factor receptor-tyrosine kinase inhibitors (EGFR-TKIs) fail due to tumor resistance, followed by disease progression.

Thus there exists a need in a field for improved systems and methods for the prognosis, diagnosis or treatment of lung cancer.

SUMMARY OF THE INVENTION

Various embodiments include a method of treating a disease in a subject, comprising providing a composition comprising one more G2/M checkpoint inhibitors, and administering to the subject a therapeutically effective dosage of the composition. In another embodiment, the disease is cancer. In another embodiment, the subject has a liver kinase B1 (LKB1) deficiency. In another embodiment, the disease is adenocarcinoma. In another embodiment, the disease is lung cancer. In another embodiment, the lung cancer is non-small cell lung cancer. In another embodiment, the G2/M checkpoint inhibitor is a Wee1 kinase inhibitor. In another embodiment, the Wee1 kinase inhibitor is AZD1775. In another embodiment, the method further comprises administering to the subject a second pharmaceutical composition. In another embodiment, the second pharmaceutical composition comprises at least one of the following: a DNA-damaging compound and a DNA repair-inhibiting compound. In another embodiment, the second pharmaceutical composition comprises at least one of cisplatin, carboplatin, pemetrexed, gemcitabine, or a combination thereof.

Other embodiments include a method of treating a subject, comprising obtaining a sample from the subject, assaying the sample to determine a presence or absence of a liver kinase B1 (LKB1) deficiency, and administering a therapeutically effective dosage of composition comprising one or more G2/M checkpoint inhibitors based on the presence of an LKB1 deficiency. In another embodiment, the subject has adenocarcinoma. In another embodiment, the subject has lung cancer. In another embodiment, the lung cancer is non-small cell lung cancer. In another embodiment, the G2/M checkpoint inhibitor is a Wee1 kinase inhibitor. In another embodiment, the Wee1 kinase inhibitor is AZD1775. In another embodiment, the method further comprises administering a therapeutically effective amount of a second pharmaceutical composition. In another embodiment, the second pharmaceutical composition comprises at least one of the following: a DNA-damaging compound and a DNA repair-inhibiting compound. In another embodiment, the composition is administered intravenously.

Other embodiments include a method of treating cancer in a subject, comprising determining the presence of one or more biomarkers indicative of an abnormal LKB1 signaling, and administering a therapeutically effective dosage of a composition comprising one or more cancer treatments. In another embodiment, the one or more cancer treatments includes a Wee1 inhibitor. In another embodiment, the abnormal LKB1 signaling includes an LKB1 deficiency. In another embodiment, the one or more cancer treatments includes at least one of cisplatin, carboplatin, pemetrexed, gemcitabine, or a combination thereof.

Various embodiments include a method of prognosing a condition in a subject, comprising obtaining a sample from the subject, assaying the sample to determine a presence or absence of a liver kinase B1 (LKB1) deficiency, and prognosing a severe form of the condition based on the presence of an LKB1 deficiency. In another embodiment, the condition is adenocarcinoma. In another embodiment, the condition is non-small cell lung cancer.

Other embodiments include a pharmaceutical composition, comprising one or more G2/M checkpoint inhibitors, and a pharmaceutically acceptable carrier.

Other features and advantages of the invention will become apparent from the following detailed description, taken in conjunction with the accompanying drawings, which illustrate, by way of example, various embodiments of the invention.

DESCRIPTION OF THE DRAWINGS

Exemplary embodiments are illustrated in referenced figures. It is intended that the embodiments and figures disclosed herein are to be considered illustrative rather than restrictive.

As illustrated in FIG. 2A, the cells transfected with the rescue copy of LKB1 were less sensitive to AZD1775, as measured by percent viability, compared to cells that were transfected with the control non-functional kinase version of LKB1.

As illustrated in FIG. 2B, the cells transfected with the rescue copy of LKB1 were less sensitive to AZD1775, as measured by percent viability, compared to cells that were transfected with the control non-functional kinase version of LKB1.

As illustrated in FIG. 2C, the cells transfected with the rescue copy of LKB1 were less sensitive to AZD1775, as measured by percent viability, compared to cells that were transfected with the control non-functional kinase version of LKB1.

FIG. 2D illustrates that the cells transfected with the rescue copy of LKB1 were less sensitive to AZD1775, as measured by percent viability, compared to cells that were transfected with the control empty vector.

DETAILED DESCRIPTION

Figure 1A:
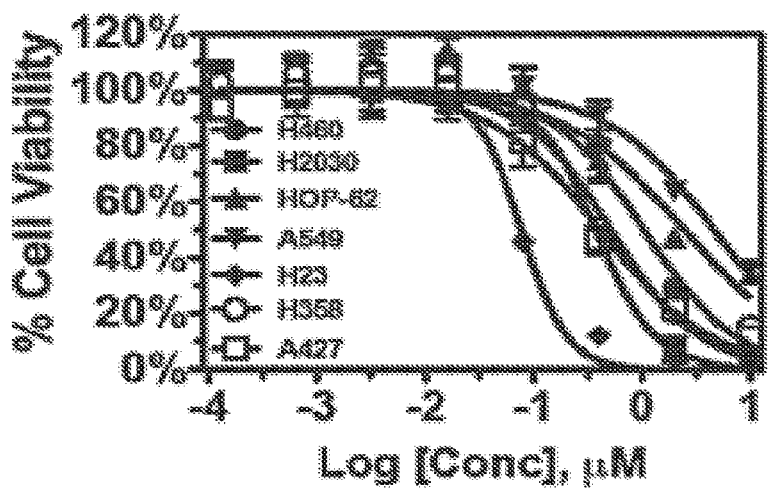
FIG. 1A illustrates, in accordance with embodiments herein, the impact of various concentrations of a G2/M checkpoint inhibitor, AZD1775, on various cell lines with different genetic backgrounds. LKB1 deficient cells had the greatest reduced viability.

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, NY 2001); March, Advanced Organic Chemistry Reactions, Mechanisms and Structure 7th ed., J. Wiley & Sons (New York, NY 2013); and Sambrook and Russel, Molecular Cloning: A Laboratory Manual 4th ed., Cold Spring Harbor Laboratory Press (Cold Spring Harbor, NY 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

One skilled in the art will recognize many methods and materials similar or equivalent to those described herein, which could be used in the practice of the present invention. Indeed, the present invention is in no way limited to the methods and materials described.

Some embodiments of the invention provide a method of treating cancer cells in a subject. In some embodiments, the cancer cells are LKB1 deficient and the method may include contacting the LKB1 deficient cancer cells with a therapeutically effective amount of a G2/M checkpoint inhibitor. In some embodiments, the cancer may comprise an adenocarcinoma, such as lung cancer. For example, the lung cancer may comprise non-small cell lung cancer. Moreover, in some embodiments, the G2/M checkpoint inhibitor may comprise a Wee1 kinase inhibitor, such as AZD1775. In addition, in some embodiments, the method may also include contacting the cells that are LKB1 deficient with a therapeutically effective amount of a second pharmaceutical composition. In some aspects, the second pharmaceutical composition may comprise at least one of the following: a DNA-damaging compound and a DNA repair-inhibiting compound. In other aspects, the second pharmaceutical composition may comprise at least one of cisplatin, carboplatin, pemetrexed, gemcitabine, and a combination thereof.

Some embodiments of the invention may include a method of treating adenocarcinoma cells in a subject, with may include the steps of (i) receiving a sample of the adenocarcinoma cells; (ii) determining if at least a portion of the sample of the adenocarcinoma cells is LKB1 deficient; and (iii) contacting the adenocarcinoma cells with a therapeutically effective amount of a G2/M checkpoint inhibitor. In some embodiments, the adenocarcinoma is lung cancer. For example, the lung cancer may comprise non-small cell lung cancer. Moreover, in some embodiments, the G2/M checkpoint inhibitor may comprise a Wee1 kinase inhibitor, such as AZD1775. In addition, in some embodiments, the method may also include contacting the cells that are LKB1 deficient with a therapeutically effective amount of a second pharmaceutical composition. In some aspects, the second pharmaceutical composition may comprise at least one of the following: a DNA-damaging compound and a DNA repair-inhibiting compound. In some particular aspects, the therapeutically effective amount of the second pharmaceutical composition is less than an amount that would be used without the G2/M checkpoint inhibitor.

Some further embodiments of the invention provide a method of treating adenocarcinoma cells in a subject. In some aspects, the adenocarcinoma cells are LKB1 deficient. The methodology may include contacting the LKB1 deficient adenocarcinoma cells with a therapeutically effective amount of a Wee1 inhibitor (e.g., AZD1775) and contacting the LKB1 deficient cancer cells with a therapeutically effective amount of a second pharmaceutical composition. In some embodiments, the adenocarcinoma is lung cancer. For example, the lung cancer may comprise non-small cell lung cancer. In some aspects, the second pharmaceutical composition may comprise at least one of the following: a DNA-damaging compound and a DNA repair-inhibiting compound. In other aspects, the second pharmaceutical composition may comprise at least one of cisplatin, carboplatin, pemetrexed, gemcitabine, and a combination thereof.

Some embodiments of the invention provide methods of treating a disease, such as cancer. For example, some embodiments of the invention include methods of treating the cancer. In some aspects, the cancer may comprise a specific form of cancer, such as adenocarcinoma. In some embodiments, the adenocarcinoma may be a specific form of cancer, such as lung cancer, which may further include non-small cell lung cancer. In some specific aspects, the methods may include detecting and/or quantifying, and/or augmenting the presence and/or activity of one or more markers. In some embodiments of the invention, the marker may comprise one or more of LKB1, RAS (e.g., KRas), and/or Wee1. In particular, some embodiments include augmenting (e.g., increasing or decreasing) a level of expression and/or functionality of the one or more markers and then providing one or more therapeutics to a patient to treat the cancer. In some aspects, some embodiments include making therapeutic decisions based at least partially upon a determination of expression and/or functionality of one or more markers (e.g., LKB1).

The present invention can be directed to methods for treating cancer. For example, methods according to some embodiments may comprise providing therapeutically effective amounts of one or more pharmaceutical compositions, alone or in combination, to the subject with cancer. In some aspects, the method may include administering one or more pharmaceutical compositions, alone or in combination, that can function to inhibit one or more markers, such as Wee1. In particular, the administration of one or more pharmaceutical compositions may inhibit one or more cellular processes such as the G2/M phase of the cell cycle. For example, a first pharmaceutical composition(s) can inhibit the G2/M phase of the cell cycle and a second composition can be administered to the subject with cancer that can potentially induce apoptosis, necrosis, and/or cellular senescence in the cancer (e.g., a DNA-damaging composition).

Some embodiments of the invention provide methods of treating cancer in a subject, which include an assessment of one or more markers to select a treatment. The method may include assessing an expression level of one or more of the markers to make determinations regarding the appropriate therapeutic decisions. For example, prior to the administration of one or more pharmaceutical compositions, an assessment of a marker (i.e., LKB1 and/or KRas) can be performed to determine whether a G2/M checkpoint inhibitor (e.g., a Wee1 kinase inhibitor) is an appropriate therapeutic. In some aspects, the assessment of the marker may include a determination regarding the expression level of the marker and in other aspects, the assessment may include making a determination of the functionality of the gene, RNA, and/or protein version(s) of the marker.

Generally, some embodiments of the present invention can be used to identify, quantify, detect, assess, isolate, and/or augment expression levels of one or more markers. A marker may be any molecular structure produced by a cell, expressed inside the cell, accessible on the cell surface, or secreted by the cell. A marker may be any protein, carbohydrate, fatty acid, nucleic acid, catalytic site, or any combination of these such as an enzyme, glycoprotein, cell membrane, virus, a particular cell, or other uni- or multi-molecular structure. A marker may be represented by a sequence of a nucleic acid or any other molecules derived from the nucleic acid. Examples of such nucleic acids include miRNA, tRNA, siRNA, mRNA, cDNA, genomic DNA sequences, or complementary sequences thereof. Alternatively, a marker may be represented by a protein sequence. The concept of a marker is not limited to the exact nucleic acid sequence or protein sequence or products thereof, rather it encompasses all molecules that may be detected by a method of assessing the marker. Without being limited by the theory, the detection of the marker may encompass the detection and/or determination of a change in copy number (e.g., copy number of a gene or other forms of nucleic acid) or in the detection of one or more translocations.

Therefore, examples of molecules encompassed by a marker represented by a particular sequence further include alleles of the gene used as a marker. An allele includes any form of a particular nucleic acid that may be recognized as a form of the particular nucleic acid on account of its location, sequence, or any other characteristic that may identify it as being a form of the particular gene. Alleles include but need not be limited to forms of a gene that include point mutations, silent mutations, deletions, frame shift mutations, single nucleotide polymorphisms (SNPs), inversions, translocations, heterochromatic insertions, and differentially methylated sequences relative to a reference gene, whether alone or in combination.

In some embodiments of the invention, the marker may comprise a plurality of markers. For example, the plurality of markers may include one or more molecules that are known to play a role in oncogenesis and/or the progression of cancer. In some aspects, the markers may comprise molecules such as LKB1, Wee1, and/or a member of the Ras family, such as KRas. In some embodiments, a combination of one or more of the above-described potential markers can be looked at in combination with other markers to provide therapeutic information for one skilled in the art in the context of one or more cancers, for example, non-small cell lung cancer (NSCLC).

The LKB1 tumor suppressor gene is commonly mutated in NSCLC, and offers a therapeutic opportunity. The LKB1 gene was discovered through genetic linkage analysis of the familial disorder, Peutz-Jeghers syndrome, and has since been found to be inactivated in 30%-50% of NSCLC patients, about twice the prevalence of EGFR mutations found in this disease. Further, convergent in vitro and in vivo studies have led to the realization that loss of LKB1 may be a critical event in NSCLC.

LKB1 (also known as STK11 serine/threonine kinase 11) is a serine-threonine kinase, phosphorylating and regulating 14 different protein kinases. The biological role of LKB1 regulation of these kinases remains largely unknown except for the AMP-activated kinase, or AMPK. The primary function of LKB1-AMPK signaling is in the regulation of cellular energy metabolism. Increases in intracellular levels of AMP, due to hypoxia, ischemia, or other stressors, induce the LKB1 dependent activation of AMPK, allowing AMPK to alter cellular functions and restore ATP levels within the cell.

There is a link between the loss of LKB1 and increased aggressiveness of adenocarcinomas such as NSCLC, colorectal adenoma, prostate and endometrial adenomas. In human endometrial cancers, LKB1 expression was found inversely correlated with tumor grade and stage, implying that LKB1 inactivation or down-regulation also contributes to endometrial cancer progression in women.

LKB1 is a tumor suppressor, yet somatic mutations to LKB1 appear to be rare in most sporadic cancers. However, recent work has shown that in lung carcinomas, mutational loss of LKB1 occurs in about 30% to about 50% of cases. NSCLC is a heterogeneous disease consisting of large cell carcinoma (LCC), adenocarcinoma, squamous cell carcinoma (SCC) and mixed histology tumors (adenosquamous). Among these subtypes, LKB1 loss appears to occur most frequently in adenocarcinoma (34%), with LKB1 loss occurring in SCC (19%), LCC (14%) and adenosquamous (25%) at lower rates.

Further, LKB1 loss synergistically cooperates with oncogenic gene KRAS to decrease tumor latency and increase tumor metastasis in a transgenic mouse model of lung cancer. KRas is involved primarily in regulating cell division. The protein relays signals from outside the cell to the cell nucleus. These signals instruct the cell to grow and divide or to mature and take on specialized functions (differentiate).

The KRas protein is a GTPase that converts GTP into GDP. The KRas protein acts like a switch, and it is turned on and off by the GTP and GDP molecules. To transmit signals, the KRas protein must be turned on by binding to a molecule of GTP. The KRas protein is turned off (inactivated) when it converts the GTP to GDP. When the protein is bound to GDP, it does not relay signals to the cell nucleus.

Mechanistically, LKB1 functions at the center of a complex signaling network, phosphorylating and activating 14 protein kinases. The best characterized of the LKB1 activated kinases is the AMP-activated kinase, or AMPK. The primary function of LKB1-AMPK signaling is in the regulation of cellular energy metabolism. Increases in intracellular levels of AMP due to hypoxia or ischemia, induce the LKB1 dependent activation of AMPK, allowing AMPK to alter cellular functions and restore ATP levels within the cell.

After DNA damage, cell cycle checkpoints are activated. Checkpoint activation pauses the cell cycle and gives the cell time to repair the damage before continuing to divide. If the damage is too severe, apoptosis or senescence is induced to ensure that unrepaired DNA-damage is not passed on to future generations of cells. Loss of checkpoint mechanisms is frequently found in cancer, a trait which can be exploited in cancer therapy. Wee1 is a kinase involved in checkpoint regulation that in response to DNA-damage or replication stress can halt the cell cycle progression in S- and G2 phases by adding inhibitory phosphorylations (Tyr15) on cyclin-dependent kinases CDK2 and CDK1, respectively. Previous studies have found that Wee1 is up-regulated in some cancers, such as melanoma, and that high expression of Wee1 was associated with poor disease-free survival. Likewise, over-expression of Wee1 (protein and/or mRNA) has been reported in osteosarcoma, glioblastoma and ovarian- and vulvar squamous cell carcinomas, thus emphasizing its potential as a therapeutic target in cancer.

An allele of a gene may or may not produce a functional protein; may produce a protein with altered function, localization, stability, dimerization, or protein-protein interaction; may have overexpression, under-expression or no expression; may have altered temporal or spatial expression specificity; or may have altered copy number (e.g., greater or less numbers of copies of the allele). An allele may also be called a mutation or a mutant. An allele may be compared to another allele that may be termed a wild type form of an allele. In some cases, the wild type allele is more common than the mutant.

Some embodiments of the invention may comprise the use of one or more methods of amplifying a nucleic acid-based starting material (i.e., a template). Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with QB replicase, whole genome amplification with enzymes such as q29, whole genome PCR, in vitro transcription with T7 RNA polymerase or any other RNA polymerase, or any other method by which copies of a desired sequence are generated.

In addition to genomic DNA, any oligonucleotide or polynucleotide sequence can be amplified with an appropriate set of primer molecules. In particular, the amplified segments created by the PCR process itself are, themselves, efficient templates for subsequent PCR amplifications. In some embodiments, the first and/or the second reagents may comprise one or more oligonucleotides (e.g., primers) that can specifically bind to DNA, RNA, and/or cDNA to detect the presence and/or expression of nucleic acids that correspond to one of the markers (e.g., LKB1 and/or KRas) using techniques such as PCR, qPCR, qRT-PCR, northern blot, etc.

PCR generally involves the mixing of a nucleic acid sample, two or more primers that are designed to recognize the template DNA, a DNA polymerase, which may be a thermostable DNA polymerase such as Taq or Pfu, and deoxyribose nucleoside triphosphates (dNTP's). Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified DNA. In such analyses, incorporation of fluorescent dye into the amplified strands may be detected or measured.

Alternatively, labeled probes that bind to a specific sequence during the annealing phase of the PCR may be used with primers. Labeled probes release their fluorescent tags during the extension phase so that the fluorescence level may be detected or measured. Generally, probes are complementary to a sequence within the target sequence downstream from either the upstream or downstream primer. Probes may include one or more label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent,) stain, enzyme, or nonradioactive metal. Specific examples include, but are not limited to: fluorescein, biotin, digoxigenin, alkaline phosphatese, biotin, streptavidin, $^3$H, $^{14}$C, $^{32}$P, $^{35}$S, or any other compound capable of emitting radiation, rhodamine, 4-(4'-dimethyl-amino-phenylazo) benzoic acid ("Dabcyl"); 4-(4'-dimethyl-amino-phenylazo) sulfonic acid (sulfonyl chloride) ("Dab-syl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of dyes facilitating the reading of the target amplification include, but are not limited to: CAL-Fluor Red 610, CAL-Fluor Orange 560, dR110, 5-FAM, 6FAM, dR6G, JOE, HEX, VIC, TET, dTAMRA, TAMRA, NED, dROX, PET, BHQ+, Gold540, and LIZ.PCR facilitating the reading of the target amplification.

Either primers or primers along with probes allow a quantification of the amount of specific template DNA present in the initial sample. In addition, RNA may be detected by PCR analysis by first creating a DNA template from RNA through a reverse transcriptase enzyme. The marker expression may be detected by quantitative PCR analysis facilitating genotyping analysis of the samples.

An illustrative example, using dual-labeled oligonucleotide probes in PCR reactions is disclosed in U.S. Pat. No. 5,716,784 to DiCesare. In one example of the PCR step of the multiplex Real Time-PCR/PCR reaction of the present invention, the dual-labeled fluorescent oligonucleotide probe binds to the target nucleic acid between the flanking oligonucleotide primers during the annealing step of the PCR reaction. The 5' end of the oligonucleotide probe contains the energy transfer donor fluorophore (reporter fluor) and the 3' end contains the energy transfer acceptor fluorophore (quenching fluor). In the intact oligonucleotide probe, the 3' quenching fluor quenches the fluorescence of the 5' reporter fluor. However, when the oligonucleotide probe is bound to the target nucleic acid, the 5' to 3' exonuclease activity of the DNA polymerase, e.g., Taq DNA polymerase, will effectively digest the bound labeled oligonucleotide probe during the amplification step. Digestion of the oligonucleotide probe separates the 5' reporter fluor from the blocking effect of the 3' quenching fluor. The appearance of fluorescence by the reporter fluor is detected and monitored during the reaction, and the amount of detected fluorescence is proportional to the amount of fluorescent product released. Examples of apparatus suitable for detection include, e.g. Applied Biosystems™ 7900HT real-time PCR platform and Roche's 480 LightCycler, the ABI Prism 7700 sequence detector using 96-well reaction plates or GENEAMP PC System 9600 or 9700 in 9600 emulation mode followed by analysis in the ABA Prism Sequence Detector or TAQMAN LS-50B PCR Detection System. The labeled probe facilitated multiplex Real Time-PCR/PCR can also be performed in other real-time PCR systems with multiplexing capabilities.

"Amplification" is a special case of nucleic acid replication involving template specificity. Amplification may be a template-specific replication or a non-template-specific replication (i.e., replication may be specific template-dependent or not). Template specificity is here distinguished from fidelity of replication (synthesis of the proper polynucleotide sequence) and nucleotide (ribo- or deoxyribo-) specificity. Template specificity is frequently described in terms of "marker" specificity. Marker sequences are "markers" in the sense that they are sought to be sorted out from other nucleic acid. Amplification techniques have been designed primarily for this sorting out.

The term "template" refers to nucleic acid originating from a sample that is analyzed for the presence of a marker of interest. In contrast, "background template" or "control"

is used in reference to nucleic acid other than sample template that may or may not be present in a sample. Background template is most often inadvertent. It may be the result of carryover, or it may be due to the presence of nucleic acid contaminants sought to be purified out of the sample. For example, nucleic acids from organisms other than those to be detected may be present as background in a test sample.

In addition to primers and probes, template specificity is also achieved in some amplification techniques by the choice of enzyme. Amplification enzymes are enzymes that, under the conditions in which they are used, will process only specific sequences of nucleic acid in a heterogeneous mixture of nucleic acid. Other nucleic acid sequences will not be replicated by this amplification enzyme. Similarly, in the case of T7 RNA polymerase, this amplification enzyme has a stringent specificity for its own promoters (Chamberlin et al. (1970) Nature (228): 227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics (4): 560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) PCR Technology, Stockton Press).

The term "amplifiable nucleic acid" refers to nucleic acids that may be amplified by any amplification method. It is contemplated that "amplifiable nucleic acid" will usually comprise "sample template." The terms "PCR product," "PCR fragment," and "amplification product" refer to the resultant mixture of compounds after two or more cycles of the PCR steps of denaturation, annealing and extension. These terms encompass the case where there has been amplification of one or more segments of one or more target sequences.

In some forms of PCR assays, quantification of a target in an unknown sample is often required. Such quantification is often in reference to the quantity of a control sample. The control sample DNA may be co-amplified in the same tube in a multiplex assay or may be amplified in a separate tube. Generally, the control sample contains DNA at a known concentration. The control sample DNA may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithm.

The algorithm for Ct values in real time-PCR calculates the cycle at which each PCR amplification reaches a significant threshold. The calculated Ct value is proportional to the number of target copies present in the sample, and the Ct value is a precise quantitative measurement of the copies of the target found in any sample. In other words, Ct values represent the presence of respective target that the primer sets are designed to recognize. If the target is missing in a sample, there should be no amplification in the Real Time-PCR reaction.

Alternatively, the Cp value may be utilized. A Cp value represents the cycle at which the increase of fluorescence is highest and where the logarithmic phase of a PCR begins. The LightCycler® 480 Software calculates the second derivatives of entire amplification curves and determines where this value is at its maximum. By using the second-derivative algorithm, data obtained are more reliable and reproducible, even if fluorescence is relatively low.

The various and non-limiting embodiments of the PCR-based method detecting marker expression level as described herein may comprise one or more probes and/or primers. Generally, the probe or primer contains a sequence complementary to a sequence specific to a region of the nucleic acid of the marker gene. A sequence having less than 60% 70%, 80%, 90%, 95%, 99% or 100% identity to the identified gene sequence may also be used for probe or primer design if it is capable of binding to its complementary sequence of the desired target sequence in marker nucleic acid.

An oligonucleotide may be any polynucleotide of at least 2 nucleotides. Oligonucleotides may be less than 10, 15, 20, 30, 40, 50, 75, 100, 200, or 500 nucleotides in length. While oligonucleotides are often linear, they may assume a circular or other two dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. In some aspects of the invention, an oligonucleotide may be 2 to 1000 bases in length. In other aspects, it may be 5 to 500 bases in length, 5 to 100 bases in length, 5 to 50 bases in length, or 10 to 30 bases in length. One skilled in the art would understand the length of oligonucleotide necessary to perform a particular task. Oligonucleotides may be directly labeled, used as primers in PCR or sequencing reactions, or bound directly to a solid substrate as in oligonucleotide arrays. For example, as described in greater detail herein, in some aspects of the invention, a first reagent can be used to detect c-Met and a second reagent can be used to detect Fn14. In some embodiments, the first and/or the second reagents may comprise one or more oligonucleotides (e.g., primers) that can specifically bind to DNA, RNA, and/or cDNA to detect the presence and/or expression of nucleic acids that correspond to one or more markers (e.g., LKB1 and/or KRas) using techniques such as PCR, qPCR, qRT-PCR, northern blot, etc.

Some embodiments of the invention may include assessing, determining, quantifying, or altering the expression of a marker. As used herein expression encompasses any and all processes through which material derived from a nucleic acid template may be produced. Expression thus includes RNA transcription, mRNA splicing, protein translation, protein folding, post-translational modification, membrane transport, associations with other molecules, addition of carbohydrate moieties to proteins, phosphorylation, protein complex formation and any other process along a continuum that results in biological material derived from genetic material. Expression also encompasses all processes through which the production of material derived from a nucleic acid template may be actively or passively suppressed. Such processes include all aspects of transcriptional and translational regulation. Examples include heterochromatic silencing, transcription factor inhibition, any form of RNAi silencing, microRNA silencing, small interfering RNA silencing, alternative splicing, protease digestion, posttranslational modification, and alternative protein folding.

Expression may be assessed by any number of methods used to detect material derived from a nucleic acid template used currently in the art and yet to be developed. Examples of such methods include any nucleic acid detection method including the following non-limiting examples, microarray analysis, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, or any other method of detecting a specific nucleic acid now known or yet to be disclosed. Other examples include any process of assessing expression that uses an antibody including the following non-limiting examples, flow cytometry, immunohistochemistry, ELISA, Western blot, and immunoaffinity chromatography. Antibodies may be monoclonal, polyclonal, or any antibody fragment including an Fab, F (ab) 2, Fv, scFv, phage display antibody, peptibody, multispecific ligand, or any other reagent with specific binding to a marker. Such methods also include direct methods used to assess protein expression including the following nonlimiting examples: HPLC, mass spectrometry, protein microarray analysis, PAGE analysis, isoelectric focusing, 2-D gel electrophoresis, and enzymatic assays. For example, as described in greater detail herein, in some aspects of the invention, a first reagent can be used to detect c-Met and a second reagent can be used to detect Fn14. In some embodiments, the first and/or the second reagents may comprise one or more antibodies that can specifically bind to protein to detect the presence and/or expression of proteins that correspond to the markers (e.g., LKB1 and/or KRas). For example, the first and second reagents in the protein context can be assessed using techniques such as immunohistochemistry, western blot analysis, flow cytometry, ELISA, and immunoaffinity chromatography. Samples from which expression may be detected include single cells, whole organs or any fraction of a whole organ, whether in vitro, ex vivo, in vivo, or post-mortem.

Other methods used to assess expression include the use of natural or artificial ligands capable of specifically binding one or more markers, including a protein, carbohydrate, fat, nucleic acid, catalytic site, or any combination of these such as an enzyme, glycoprotein, cell membrane, virus, cell, organ, organelle, or any uni- or multimolecular structure that constitutes a marker that may be specifically bound by a ligand. Such ligands include antibodies, antibody complexes, conjugates, natural ligands, small molecules, nanoparticles, or any other molecular entity capable of specific binding to a marker. Ligands may be associated with a label such as a radioactive isotope or chelate thereof, dye (fluorescent or non-fluorescent,) stain, enzyme, metal, or any other substance capable of aiding a machine or a human eye from differentiating a cell expressing a marker from a cell not expressing a marker. Additionally, expression may be assessed by monomeric or multimeric ligands associated with substances capable of killing the cell. Such substances include protein or small molecule toxins, cytokines, pro-apoptotic substances, pore forming substances, radioactive isotopes, or any other substance capable of killing a cell.

Positive expression encompasses any difference between a cell expressing markers and a cell that does not express one or more of the markers. The exact nature of positive expression varies by the method, but is well known to those skilled in the art of practicing a particular method. Positive expression may be assessed by a detector, an instrument containing a detector, or by aided or unaided human eye. Examples include but are not limited to specific staining of cells expressing a target in an IHC slide, binding of RNA from a sample to a microarray and detection of binding through the use of said microarray, a particular rate of dye incorporation in real-time RTPCR measured in ACt or alternatively in the number of PCR cycles necessary to reach a particular optical density at a wavelength at which a double stranded DNA binding dye (e.g. SYBR Green) incorporates, through release of label from a previously labeled reporter probe used in a real-time RTPCR reaction, detection of fluorescence on a cell expressing a target by a flow cytometer, the presence of radiolabeled bands on film in a Northern blot, detection of labeled blocked RNA by RNAse protection assay, cell death measured by apoptotic markers, cell death measured by shrinkage of a tumor, or any other signal for the expression of a marker in existence now or yet to be developed. In some aspects of the invention, positive expression is a sufficient level of expression to correlate with a particular response such as susceptibility to cancer recurrence.

In some aspects of the invention, reduced expression constitutes no detectable expression. However, the concept of reduced expression further encompasses insufficient expression to reach or exceed a threshold, cutoff, or level that has been previously shown to result in a particular cellular or physiological response. Reduced expression may include similar expression relative to a control that has been previously determined not to express the marker(s) or similar expression to a control that has been previously determined not to exhibit the response. In this case, even though expression may be detectable, it still constitutes reduced expression. In some aspects of the invention, an expression level of a marker in a control known to have a reduced or increase risk of recurrence is predetermined and expression similar to that level is correlated with reduced or increase risk of recurrence. Increased or reduced expression includes expression that is 75% 50%, 25%, 10%, 5%, 1%, 0.1%, greater or less of that of a control cell or a median level of expression in a population. Reduced expression may also include greater than or less than $1 \times 10^{-5}$ greater or less expression normalized to the expression of a housekeeping gene.

The invention contemplates assessing the expression of the marker(s) in any biological sample from which the expression may be assessed. One skilled in the art would know to select a particular biological sample and how to collect said sample depending upon the marker that is being assessed. Examples of sources of samples include but are not limited to biopsy or other in vivo or ex vivo analysis of prostate, breast, skin, muscle, fascia, brain, endometrium, lung, head and neck, pancreas, small intestine, blood, liver, testes, ovaries, colon, skin, stomach, esophagus, spleen, lymph node, bone marrow, kidney, placenta, or fetus. In some aspects of the invention, the sample comprises a fluid sample, such as peripheral blood, lymph fluid, ascites, serous fluid, pleural effusion, sputum, cerebrospinal fluid, amniotic fluid, lacrimal fluid, stool, or urine. In one aspect of the invention, the sample comprises primary or metastatic NSCLC cells. In another, the sample comprises sputum. In another aspect of the invention, the sample comprises blood or other tissues obtained from a subject who has been diagnosed with or is suspected of having NSCLC.

Assessing the risk of a particular disease outcome includes the performing of any type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to survival, death, progression of existing disease, remission of existing disease, initiation of onset of a disease in an otherwise disease-free subject, or the continued lack of disease in a subject in which there has been a remission of disease. Assessing the risk of a particular disease encompasses diagnosis in which the type of disease afflicting a subject is determined. Assessing the risk of a disease outcome also encompasses the concept of prognosis. A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

The sample in this method is preferably a biological sample from a subject. The term "sample" or "biological sample" is used in its broadest sense. Depending upon the embodiment of the invention, for example, a sample may comprise a bodily fluid including whole blood, serum, plasma, urine, saliva, cerebral spinal fluid, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a tissue; a tissue print, or any other material isolated in whole or in part from a living subject. Biological samples may also include sections of tissues such as biopsy and autopsy samples, and frozen sections taken for histologic purposes such as blood, plasma, serum, sputum, stool, tears, mucus, hair, skin, and the like. Biological samples also include explants and primary and/or transformed cell cultures derived from patient tissues.

The term "subject" is used in its broadest sense. In a preferred embodiment, the subject is a mammal. Non-limiting examples of mammals include humans, dogs, cats, horses, cows, sheep, goats, and pigs. Preferably, a subject includes any human or non-human mammal, including for example: a primate, cow, horse, pig, sheep, goat, dog, cat, or rodent, capable of developing cancer including human patients that are suspected of having cancer, that have been diagnosed with cancer, or that have a family history of cancer.

Some embodiments of the invention may include a method of comparing a marker in a sample relative to one or more control samples. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources.

Cancer cells include any cells derived from a tumor, neoplasm, cancer, precancer, cell line, malignancy, or any other source of cells that have the potential to expand and grow to an unlimited degree. Cancer cells may be derived from naturally occurring sources or may be artificially created. Cancer cells may also be capable of invasion into other tissues and metastasis. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Examples of cancers that could serve as sources of cancer cells include solid tumors such as fibrosarcoma, myxosarcoma, liposarcoma, chondrosarcoma, osteogenic sarcoma, chordoma, angiosarcoma, endothelio sarcoma, lymphangiosarcoma, lymphangioendothelio sarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may serve as sources of cancer cells include blood borne cancer, such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

In some aspects of the invention, the cancer cells are derived from NSCLC, which comprises any carcinoma derived from lung tissues that does not include small cell lung cancers. Examples of non-small cell lung cancers include adenocarcinomas, large cell carcinomas, and squamous cell carcinomas of the lung.

The pathologic stages of non-small cell lung cancer include, but are not limited to the following: in the occult or hidden stage, cancer cells may be found in sputum, but no tumor can be found in the lung by bronchoscopy or other imaging. In Stage 0, also called carcinoma in situ, abnormal cells are found in the innermost lining of the lung. Such abnormal cells are precancerous and may or may not become malignant and spread into nearby tissue.

In Stage I, a cancer has developed. There are two substages to stage 1. In Stage IA, the tumor presents only in the lung only and is 3 centimeters or smaller. For the disease to be considered stage 1B, it will have one or more of the following traits: the tumor is larger than 3 centimeters, the cancer has spread to the main bronchus of the lung, and is at least 2 centimeters from the carina, the cancer has spread to the innermost layer of the membrane that covers the lungs, or the tumor partly blocks the bronchus or bronchioles and part of the lung has collapsed or developed pneumonitis (inflammation of the lung).

Similarly, there are two substages to Stage II. In Stage IIA, the tumor is 3 centimeters or smaller and cancer has spread to nearby lymph nodes on the same side of the chest as the tumor. For the disease to be considered, Stage IIB, the cancer has spread to nearby lymph nodes on the same side of the chest as the tumor and it will have one or more of the following traits: the tumor is larger than 3 centimeters, the cancer has spread to the main bronchus of the lung and is 2 centimeters or more from the carina, the cancer has spread to the innermost layer of the membrane that covers the lungs, or the tumor partly blocks the bronchus or bronchioles and part of the lung has collapsed or developed pneumonitis (inflammation of the lung). Alternatively, the disease may be classified as Stage 2B if the cancer has not spread to the lymph nodes and it displays one or more of the following traits: cancer has spread to the chest wall, or the diaphragm, or the pleura between the lungs, or membranes surrounding the heart, the cancer has spread to the main bronchus of the lung and is no more than 2 centimeters from the carina, but has not spread to the trachea, cancer blocks the bronchus or bronchioles and the whole lung has collapsed or developed pneumonitis (inflammation of the lung). Stage III is also divided into two substages.

In stage IIIA, cancer has spread to lymph nodes on the same side of the chest as the tumor and it displays one or more of the following traits: cancer has spread to the main bronchus, the chest wall, the diaphragm, the pleura around the lungs, or the membrane around the heart, but has not spread to the trachea, or part or all of the lung may have collapsed or developed pneumonitis (inflammation of the lung). In stage IIIB, the tumor has spread to one or more of the following: lymph nodes above the collarbone or in the opposite side of the chest from the tumor, to the heart, to major blood vessels that lead to or from the heart, to the chest wall, to the diaphragm, to the trachea, to the esophagus, to the sternum or spine, to more than one area in the same lobe of the lung, or to the fluid of the pleural cavity surrounding the lung.

In stage IV, cancer may have spread to lymph nodes and has spread to another lobe of the lung or to other parts of the body, such as the brain, liver, adrenal glands, kidneys, or bone.

The present invention further provides kits to be used in assessing the expression of a marker in a subject to assess the risk of developing disease, diagnosing the subject as having a stage of the disease, or determining to which stage the disease has progressed. Kits include any combination of components that facilitates the performance of an assay. A kit that facilitates assessing the expression of the markers may include suitable nucleic acid-based and immunological reagents as well as suitable buffers, control reagents, and printed protocols.

Kits that facilitate nucleic acid based methods may further include one or more of the following: specific nucleic acids such as oligonucleotides, labeling reagents, enzymes including PCR amplification reagents such as Taq or Pfu, reverse transcriptase, or other, and/or reagents that facilitate hybridization, as previously described.

In some aspects of the invention, a probe may be affixed to a solid substrate. In other aspects of the invention, the sample may be affixed to a solid substrate. A probe or sample may be covalently bound to the substrate or it may be bound by some non-covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi-solid material onto which a probe may be affixed, attached or printed, either singly or in the formation of a microarray. Examples of substrate materials include but are not limited to polyvinyl, polystyrene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array. The sample may be bound to a substrate in the case of a Southern Blot.

As used herein "LKB1 deficient", an "LKB1 deficient patient," an "LKB1 deficient subject," and/or an "LKB1 deficiency" (all used interchangeably) refer to either (i) an inactive and/or reduced activity in the DNA, RNA, and/or protein states of LKB1 or (ii) reduced or non-detectable expression (i.e., at the transcriptional or translational level) of LKB1 such normal cellular processes that depend on LKB1 are not functioning as intended. In other words, an LKB1 deficiency is one in which LKB1 is either not sufficiently expressed at the RNA or protein level for normal cellular functioning or there is an alteration in the DNA, RNA, or amino acid sequence of LKB1 such that the resulting molecule (if any) does not properly function. Moreover, in some embodiments, LKB1 deficiency may result from a change at the DNA or RNA level such that normal cellular processes such as transcription or translation do not properly occur or do not give rise to a functional LKB1 molecule. In some embodiments, the LKB1 deficiency may be at least partially due to mutation (e.g., change in one or more synonymous and/or non-synonymous DNA bases in the LKB1 gene), deletion of some or all of the LKB1 DNA sequence on one or both chromosomes, loss of heterozygosity, and/or a specific and/or general loss of protein expression.

As used herein "G2/M checkpoint inhibitor" refers to any compound, molecule, structure, or other composition that is now known or later discovered that can function to inhibit the G2/M checkpoint. The G2/M checkpoint is known to those skilled in the art as the checkpoint through which all non-terminally differentiated cells must pass prior to entering mitosis. In some organisms, this checkpoint can be the point at which the cells survey DNA damage and cell size and can be controlled through by various molecules, such as cyclin-dependent kinases and other molecules, such as Wee1 kinase. G2/M checkpoint inhibitors can comprise any composition that is known to at least partially initiate arrest at the G2/M checkpoint. In some embodiments, the arrest at the G2/M checkpoint may be at least partially due the presence of damage to the DNA of the cell. Some examples of G2/M checkpoint inhibitors may include, but are not limited to Wee1 kinase inhibitors, Chk inhibitors, aurora kinase inhibitors, and PLK inhibitors. In some particular embodiments, the G2/M checkpoint inhibitor comprises a Wee1 kinase inhibitor.

As used herein "Wee1 kinase inhibitor" or "Wee1 inhibitor" refer to any compound, molecule, structure, or other composition that is now known or later discovered that can function to inhibit Wee1 kinase in an in vivo or an in vitro setting. In some aspects, the Wee1 inhibitor refers to a compound or pharmaceutical composition that is capable of inhibiting the expression and/or the activity of the Wee1 protein or RNA. For example, a Wee1 inhibitor may comprise a compound or composition that is capable of partially or completely interrupting the physical, chemical, electrostatic or any other interactions between Wee1 protein and any other molecules (e.g., other proteins) to inhibit the G2/M checkpoint. In particular, a Wee1 inhibitor may prevent, preclude, and/or reduce the ability of Wee1, a tyrosine kinase, to phosphorylates cyclin-dependent kinase 1 (CDC2) to inactivate the CDC2/cyclin B complex, which leads to inhibition of the G2/M checkpoint. In some aspects, a Wee1 inhibitor may inhibit or substantially reduce Wee1 expression at the transcriptional and/or translational level. For example, the Wee1 inhibitor may comprise siRNA, shRNA, and/or antibodies that target the Wee1 RNA or amino acid sequences. Some further non-limiting examples of Wee1 inhibitors include AZD1775/MK-1775 and Kruppel-like factor 2.

As used herein "DNA-damaging compound" refer to any compound, molecule, structure, or other composition that is now known or later discovered that can function to damage the DNA of a subject/patient. DNA-damaging compounds can include platinum-derived pharmaceutical (e.g., cisplatin, carboplatin, oxaliplatin etc.), methotrexate, doxorubicin, daunorubicin or the administration of radiation (e.g., ionizing radiation). The above listed agents are only illustrative in nature and any other agents can be used that exhibit DNA-damaging properties.

As used herein "DNA repair-inhibiting compound" refer to any compound, molecule, structure, or other composition that is now known or later discovered that can function to inhibit the repair of any damage to DNA. DNA repair-inhibiting compounds can include pemetrexed, gemcitabine, methylating agents (e.g., temozolomide, dacarbazine and carmustine), Alkylade®, Patrin, etc. The above listed agents are only illustrative in nature and any other agents can be used that exhibit DNA repair-inhibiting properties.

Some embodiments of the invention may include the administration of a pharmaceutical composition or a pharmacological composition to a subject that has been diagnosed with cancer. Such pharmaceutical compositions may take any physical form necessary depending on a number of factors including the desired method of administration and the physicochemical and stereochemical form taken by the compound or pharmaceutically acceptable salts of the compound. Such physical forms include a solid, liquid, gas, sol, gel, aerosol, or any other physical form now known or yet to be disclosed.

The concept of a pharmaceutical composition encompasses a compound or a pharmaceutically acceptable salt thereof with or without any other additive. The physical form of the invention may affect the route of administration and one skilled in the art would know to choose a route of administration that takes into consideration both the physical form of the compound and the disorder to be treated. Pharmaceutical compositions may be prepared using methodology well known in the pharmaceutical art.

In some aspects of the invention, the pharmaceutical composition can comprise one or more compounds or products that are capable of treating a subject with NSCLC (e.g., the treatments considered by the medical community as the "standard of care"). In some embodiments, the pharmaceutical composition may comprise or include one or more compounds that are capable of affecting the markers (e.g., Wee1). The pharmaceutical composition may comprise one or more compounds that are capable of augmenting the expression of one or more of the markers. For example, the pharmaceutical composition may comprise one or more compounds that are capable of reducing expression of one or more of the markers. In some aspects, the one or more compounds can reduce the transcription, translation, and/or post-translational processes associated generally or specifically with one or more of the markers. Moreover, in some embodiments, the pharmaceutical composition may comprise one or more compounds that can inhibit the functionality of one or more of the markers, such as Wee1.

Moreover, in some embodiments, as described in greater detail herein, the method may include the administration of a combination of pharmaceutical compositions in subjects that may be LKB1 deficient. Specifically, in some aspects, the combination may comprise the administration of a first pharmaceutical composition that inhibits one of the markers (e.g., Wee1) and a second pharmaceutical composition that can function as conventional chemotherapeutic agent (e.g., a DNA-damaging compound or a DNA repair-inhibiting compound). Moreover, in some specific embodiments, the second pharmaceutical composition may comprise a lesser concentration of the conventional chemotherapeutic agent(s), at least in part due to the activity of the first pharmaceutical composition, relative to conditions that do not include the administration of the first pharmaceutical composition.

In addition, in some aspects, one or more treatments can be provided in the event of the detection of one or more of the markers. By way of example only, in some aspects, detection of reduced expression and/or reduced/eliminated functionality of one or more of the markers (e.g., LKB1) can indicate that the subject should receive a G2/M checkpoint inhibitor (e.g., a Wee1 kinase inhibitor) possibly in combination with a second pharmaceutical composition (e.g., a DNA repair-inhibiting compound and/or a DNA-damaging compound).

Pharmaceutical compositions include materials capable of modifying the physical form of a dosage unit. In one non-limiting example, the composition includes a material that forms a coating that contains the compound. Materials that may be used in a coating, include, for example, sugar, shellac, gelatin, or any other inert coating agent.

Pharmaceutical compositions including the disclosed agents may be prepared as a gas or aerosol. Aerosols encompass a variety of systems including colloids and pressurized packages. Delivery of a composition in this form may include propulsion of a pharmaceutical composition including the disclosed compound through use of liquefied gas or other compressed gas or by a suitable pump system. Aerosols may be delivered in single phase, bi-phasic, or multi-phasic systems.

In some aspects of the invention, the pharmaceutical composition including the disclosed agents is in the form of a solvate. Such solvates are produced by the dissolution of the disclosed compound in a pharmaceutically acceptable solvent. Pharmaceutically acceptable solvents include any mixtures of one or more solvents. Such solvents may include pyridine, chloroform, propan-1-ol, ethyl oleate, ethyl lactate, ethylene oxide, water, ethanol, and any other solvent that delivers a sufficient quantity of the disclosed compound to treat the indicated condition.

Pharmaceutical compositions may also include at least one pharmaceutically acceptable carrier. Carriers include any substance that may be administered with the disclosed compound with the intended purpose of facilitating, assisting, or helping the administration or other delivery of the compound. Carriers include any liquid, solid, semisolid, gel, aerosol or anything else that may be combined with the disclosed compound to aid in its administration. Examples include diluents, adjuvants, excipients, water, and oils (including petroleum, animal, vegetable or synthetic oils.) Such carriers include particulates such as a tablet or powder, liquids such as oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or digylcerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition may take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers and formulations are well known in the art.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intranasal, intracerebral, intraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration of the disclosed compound to the area in need of treatment. Examples include local infusion during surgery; topical application, by local injection; by a catheter; by a suppository; or by an implant. Administration may be by direct injection into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include the use of an inhaler or nebulizer, formulation with an aerosolizing agent, or via perfusion in a fluorocarbon or synthetic pulmonary surfactant. Compounds may be delivered in the context of a vesicle such as a liposome or any other natural or synthetic vesicle. Additional examples of suitable modes of administration are well known in the art.

A pharmaceutical composition formulated to be administered by injection may be prepared by dissolving the disclosed compound with water so as to form a solution. In addition, a surfactant may be added to facilitate the formation of a homogeneous solution or suspension. Surfactants include any complex capable of non-covalent interaction with the disclosed compound so as to facilitate dissolution or homogeneous suspension of the compound.

Pharmaceutical compositions may be prepared in a form that facilitates topical or transdermal administration. Such preparations may be in the form of a solution, emulsion, ointment, gel base, transdermal patch or iontophoresis device. Examples of bases used in such compositions include petrolatum, lanolin, polyethylene glycols, beeswax, mineral oil, diluents such as water and alcohol, and emulsifiers and stabilizers, thickening agents, or any other suitable base now known or yet to be disclosed.

Determination of an effective and/or therapeutic amount of the disclosed agents is within the capability of those skilled in the art, especially in light of the detailed disclosure provided herein. The effective amount of a pharmaceutical composition used to affect a particular purpose as well as its toxicity, excretion, and overall tolerance may be determined in vitro, or in vivo, by pharmaceutical and toxicological procedures either known now by those skilled in the art or by any similar method yet to be disclosed. One example is the in vitro determination of the IC50 (half maximal inhibitory concentration) of the pharmaceutical composition in cell lines or target molecules. Another example is the in vivo determination of the LD50 (lethal dose causing death in 50% of the tested animals) of the pharmaceutical composition. The exact techniques used in determining an effective amount will depend on factors such as the type and physical/chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of disclosed compound for administration also includes the determination of an effective therapeutic amount and a pharmaceutically acceptable dose, including the formulation of an effective dose range for use in vivo, including in humans.

As described above, in some embodiments, the administration of a first pharmaceutical composition that may comprise a G2/M checkpoint inhibitor, such as a Wee1 kinase inhibitor, may alter that effective amount of a second pharmaceutical composition (e.g., a DNA repair-inhibiting compound and/or a DNA-damaging compound) that may be necessary to treat the subject. For example, in some aspects, the combination of the Wee1 inhibitor and the second pharmaceutical composition may provide synergistic effects such that a reduced concentration of the second pharmaceutical composition is needed to provide the same therapeutic benefits as in conditions in which the first pharmaceutical composition is omitted. As such, in these embodiments, there may be reduced side effects observed in the subject.

Treatment of a condition or disease is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease. Generally, the effectiveness of treatment is determined by comparing treated groups with non-treated groups.

The addition of a therapeutically effective amount of a compound encompasses any method of dosing of a compound. Dosing of the disclosed compound may include single or multiple administrations of any of a number of pharmaceutical compositions that include the disclosed compound as an active ingredient. Examples include a single administration of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A dosing regimen including the regularity of and mode of administration will be dependent on any of a number of factors including but not limited to the subject being treated; the severity of the condition; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

Pharmaceutical compositions may be administered prior to, concurrently with, or after administration of additional or the second pharmaceutical compositions. Concurrent administration means compositions are administered within about one minute of each other. If not administered concurrently, the additional or second pharmaceutical compositions may be administered a period of one or more minutes, hours, days, weeks, or months before or after the pharmaceutical composition that includes the currently disclosed compound. Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration. Cycling therapy may be used, for example, to reduce the development of resistance to one or more of the compositions, to avoid or reduce the side effects of one or more of the compositions, and/or to improve the efficacy of the treatment.

The invention further encompasses kits that facilitate the administration of the disclosed compound to a diseased entity. An example of such a kit includes one or more unit dosages of one or more active ingredients. The unit dosage would be enclosed in a preferably sterile container and would be comprised of the compound and a pharmaceutically acceptable carrier. In another aspect, the unit dosage would comprise one or more lyophilates of the compound. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the device comprises the container that encloses the unit dosage. In another aspect, the kit may include one or more additional compounds for administration and administration instructions therefor.

Overall, some embodiments of the invention include systems and methods for treating a condition. Particular embodiments comprise the use of one or more markers (e.g., LKB1 and/or KRAS) to make a selection of one or more pharmaceutical compositions. In some aspects, the cancer may comprise an adenocarcinoma, such as non-small cell lung cancer. For example, the method of treatment may comprise altering the expression and/or function of one or more markers (e.g., Wee1 kinase).

As used herein, the term "G2/M checkpoint" refers to a cell cycle checkpoint in eukaryotic cells which ensure proper division of the cell. Currently, there are three known checkpoints: the G1 checkpoint; the G2/M checkpoint; and the metaphase checkpoint, also known as the spindle checkpoint. Each checkpoint serves as a potential halting point along the cell cycle, during which the conditions of the cell are assessed, with progression through the various phases of the cell cycle occurring when favorable conditions are met.

Following the decision to enter the cell cycle and undergo division, the cell goes through S phase, in which it replicates its DNA, and, in most species, G2, in which it undergoes rapid growth and protein synthesis in preparation for mitosis. In some embodiments, the G2/M checkpoint, also known as the DNA damage checkpoint, ensures that the cell underwent all of the necessary changes during the S and G2 phases and is ready to divide.

Wee1 is a nuclear kinase belonging to the Ser/Thr family of protein kinases. It participates in cell cycle checkpoint by inhibiting entry of the cell into mitosis, through inhibiting the Cdk1 protein.

As used herein, the terms "AZD1775" and "MK 1775" contemplates a highly selective, potent, ATP competitive, small molecule inhibitor of Wee1 kinase. AZD1775 inhibits Wee1 activity and induces DNA damage as well as G2 checkpoint escape. In some embodiments AZD1775 or MK1775 contemplates a molecule having the chemical structure

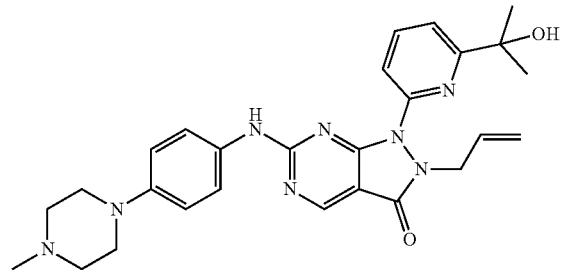 [SMILES: C=CCn1c(=O)c2cnc(Nc3ccc(N4CCN(C)CC4)cc3)nc2n1-c1cccc(C(C)(C)O)n1]

Embodiments of the present disclosure are further described in the following examples. The examples are merely illustrative and do not in any way limit the scope of the invention as claimed.

EXAMPLES

Figure 1B:
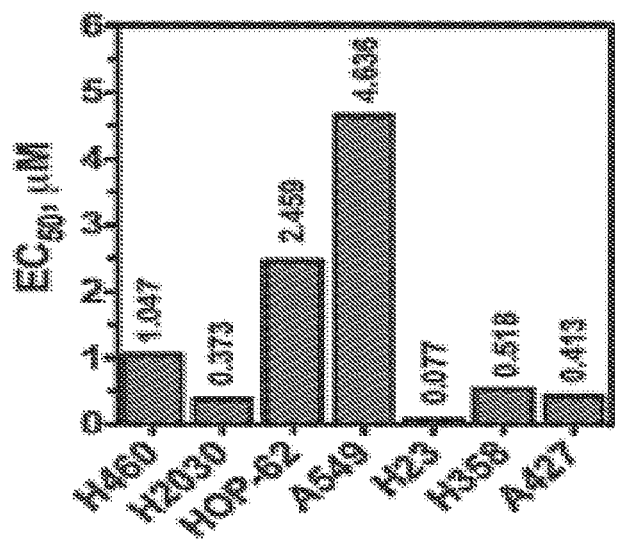
FIG. 1B illustrates, in accordance with embodiments herein, the impact of various concentrations of a G2/M checkpoint inhibitor, AZD1775, on various cell lines with different genetic backgrounds. LKB1 deficient cells had the lowest EC50 values.

Referring to FIGS. 1A and 1B, the inventors assessed the impact of various concentrations of a G2/M checkpoint inhibitor (i.e., Wee1 kinase inhibitor-AZD1775) on various cell lines with different genetic backgrounds. All of the cell lines tested in FIGS. 1A and 1B where KRas mutant, some of the cell lines were p53 mutants, and some of the cell lines (i.e., A427, A549, and H2030) were LKB1 deficient. All cell lines were adenocarcinoma from patients with NSCLC. As illustrated in these figures, the cells responded differently to increasing concentrations of AZD1775, with the LKB1 deficient cells having the greatest reduced viability (FIG. 1A) and lowest EC50 values (FIG. 1B).

Figure 2A:
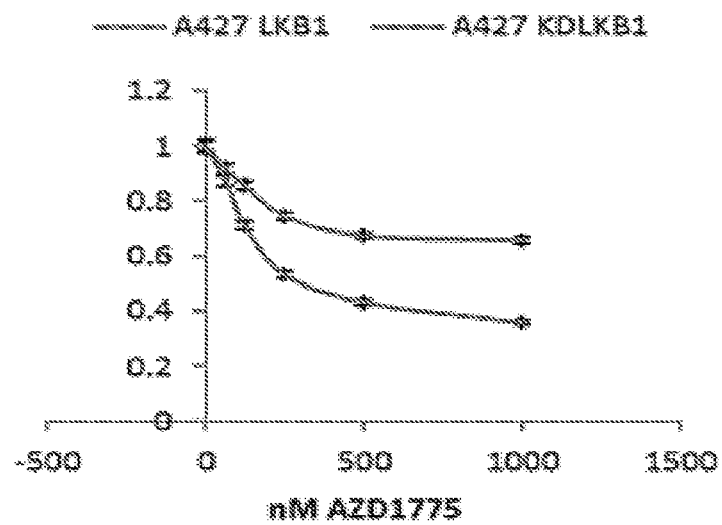
FIG. 2A illustrates, in accordance with embodiments herein, the role of LKB1 in the sensitivity of A427 cells to AZD1775. The A427 cell line was transfected with either a rescue copy of LKB1 ("LKB1") or a copy of LKB1 with a non-functional kinase domain ("KDLKB1") that produces non-functional LKB1.
Figure 2B:
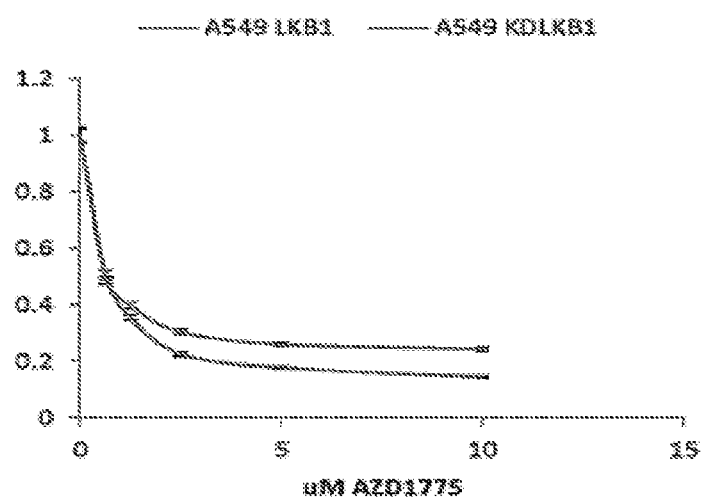
FIG. 2B illustrates, in accordance with embodiments herein, the role of LKB1 in the sensitivity of A427 cells to AZD1775. The A549 cell line was transfected with either a rescue copy of LKB1 ("LKB1") or a copy of LKB1 with a non-functional kinase domain ("KDLKB1") that produces non-functional LKB1.
Figure 2C:
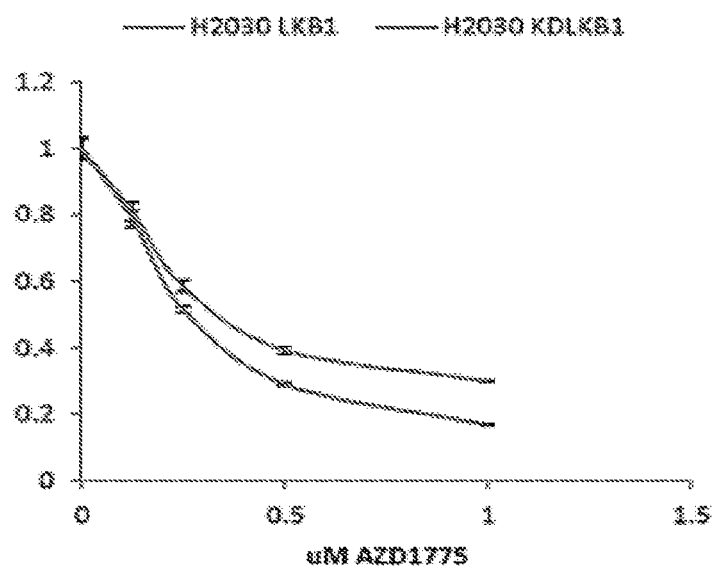
FIG. 2C illustrates, in accordance with embodiments herein, the role of LKB1 in the sensitivity of A427 cells to AZD1775. The H2030 cell line was transfected with either a rescue copy of LKB1 ("LKB1") or a copy of LKB1 with a non-functional kinase domain ("KDLKB1") that produces non-functional LKB1.

Next, referring to FIGS. 2A-2C, the LKB1 deficient lines discussed above in reference to FIGS. 1A and 1B were assessed for percent viability in the presence of increasing concentrations of AZD1775. Moreover, as all three cell lines were already LKB1 deficient, the inventors wanted to elucidate the role of LKB1 in the sensitivity of these cells to AZD1775. As such, each cell line with transfected with either a rescue copy of LKB1 (referred to as "LKB1" in these figures) or a copy of LKB1 with a non-functional kinase domain (referred to as KDLKB1 in these figures), which would produce non-functional LKB1. As illustrated in FIGS. 2A-2C, the cells transfected with the rescue copy of LKB1 were less sensitive to AZD1775, as measured by percent viability, compared to cells that were transfected with the control non-functional kinase version of LKB1.

Figure 2D:
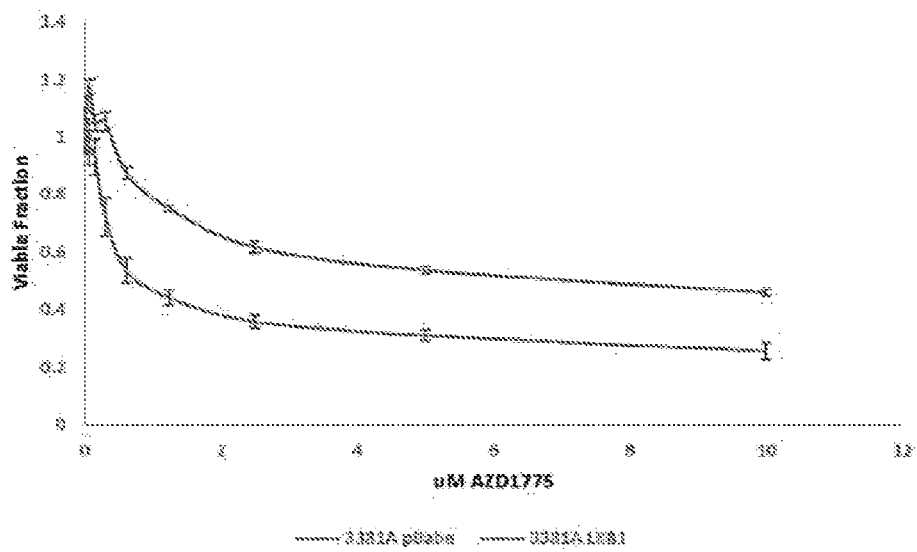
FIG. 2D illustrates, in accordance with embodiments herein, the role of LKB1 in the sensitivity of murine cells to AZD1775. 3381A murine cells (which were KRas mutant and LKB1 deficient) were transfected with either a rescue copy of LKB1 ("LKB1") or an empty vector that did not include a copy of LKB1 ("pBabe").

Referring now to FIG. 2D, a similar experiment was conducted on murine cells that were KRas mutant and LKB1 deficient (3381A cells). In these experiments, these murine cells were transfected with either a rescue copy of LKB1 (referred to as "LKB1" in FIG. 2D) or an empty vector that did not include a copy of LKB1 (referred to as pBabe in FIG. 2D). Once again, this data shows that the cells transfected with the rescue copy of LKB1 were less sensitive to AZD1775, as measured by percent viability, compared to cells that were transfected with the control empty vector. Taken together, the data in FIGS. 2A-2D illustrates that cells with an LKB1 deficiency exhibit increased sensitivity to AZD1775, as shown by decreased cell viability.

Figure 3A:
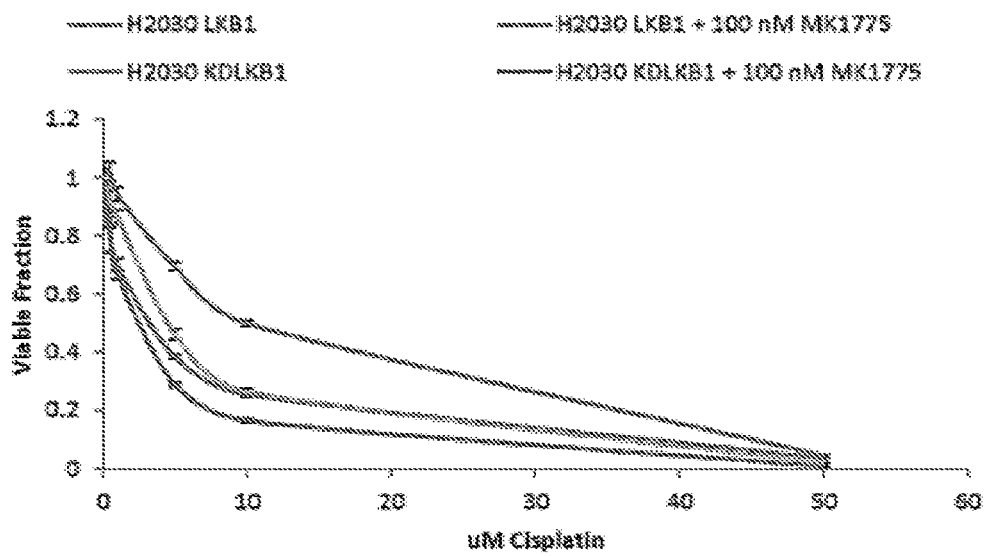
FIG. 3A illustrates, in accordance with embodiments herein, that the viability of H2030 cells (KRas mutant and LKB1 deficient) treated with AZD1775 (also referred to as MK1775) and cisplatin, is reduced when AZD1775 is combined with DNA-damaging compounds or DNA repair-inhibiting compounds.
Figure 3B:
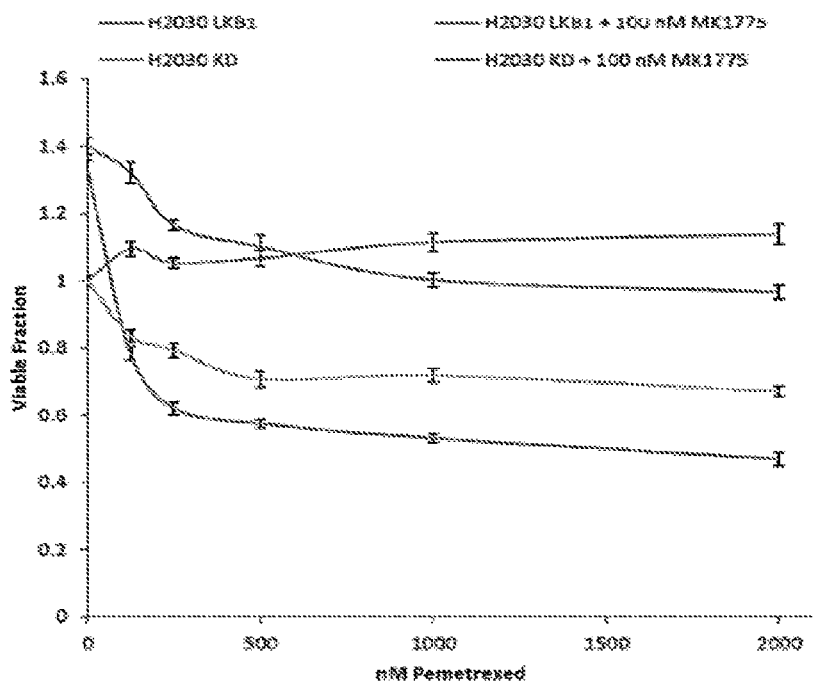
FIG. 3B illustrates, in accordance with embodiments herein, that the viability of H2030 cells (KRas mutant and LKB1 deficient) treated with AZD1775 (also referred to as MK1775) and pemetrexed, is reduced when AZD1775 is combined with DNA-damaging compounds or DNA repair-inhibiting compounds. H2030 cells were transfected with a rescue copy of LKB1 or a version of LKB1 with a non-functional kinase domain (KD) that produces non-functional LKB1 protein.
Figure 3C:
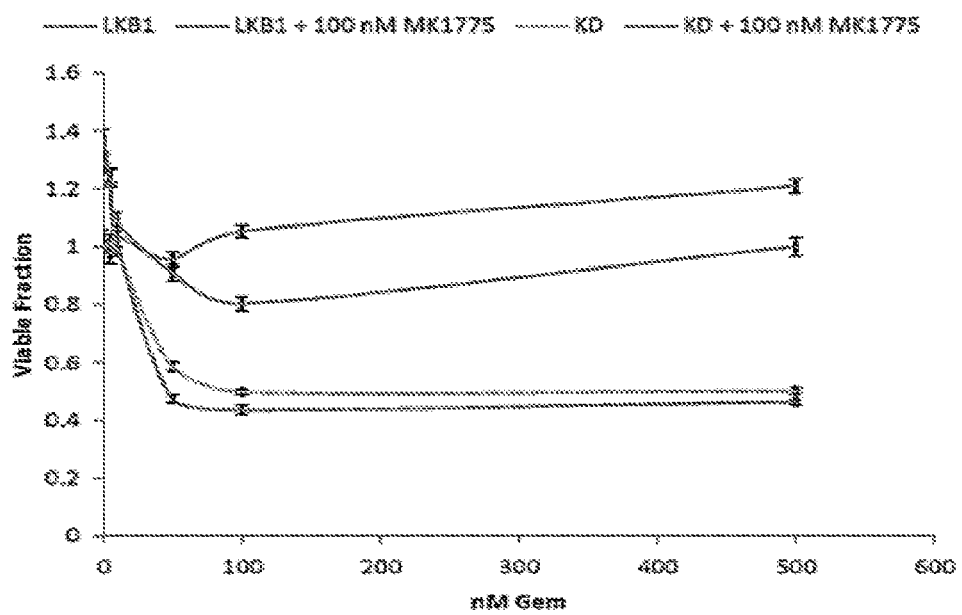
FIG. 3C illustrates, in accordance with embodiments herein, that the viability of H2030 cells (KRas mutant and LKB1 deficient) treated with AZD1775 (also referred to as MK1775) and gemcitabine, is reduced when AZD1775 is combined with DNA-damaging compounds or DNA repair-inhibiting compounds. H2030 cells were transfected with a rescue copy of LKB1 or a version of LKB1 with a non-functional kinase domain (KD) that produces non-functional LKB1 protein.
Figure 3D:
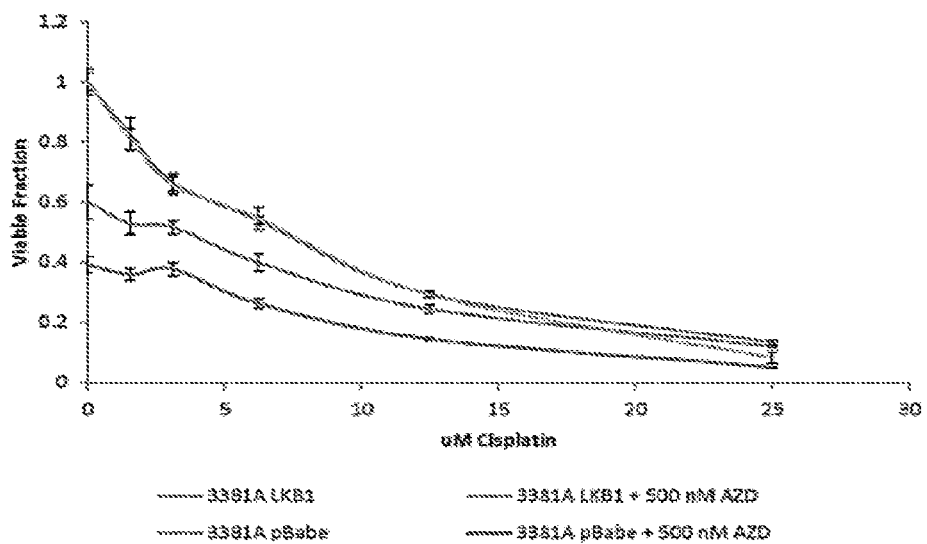
FIG. 3D illustrates, in accordance with embodiments herein, that a similar phenomenon as FIGS. 3A-C was noted in the 3381A murine cells in the case of cisplatin. Similar data was also noted with pemetrexed and gemcitabine.

Referring now to FIGS. 3A-3C, the investigators demonstrate that the combination of AZD 1775 with conventional chemotherapeutics results in a synergistic effect on the NSCLC cells. Similar to the previous experiments, H2030 cells (KRas mutant and LKB1 deficient) were transfected with a rescue copy of LKB1 or a version of LKB1 with a non-functional kinase domain that produces non-functional LKB1 protein. Moreover, these different cells were treated with AZD1775 (also referred to as MK1775) in combination with cisplatin (FIG. 3A), pemetrexed (FIG. 3B), or gemcitabine (FIG. 3C). The data in these figures demonstrates that AZD1775 has a negative impact on cell viability of the LKB1 deficient cells and that the viability of these cells is further reduced when AZD1775 is combined with DNA-damaging compounds or DNA repair-inhibiting compounds. Referring to FIG. 3D, a similar phenomenon is noted in the 3381A murine cells in the case of cisplatin; however, similar data was also noted with pemetrexed and gemcitabine.

Figure 4A:
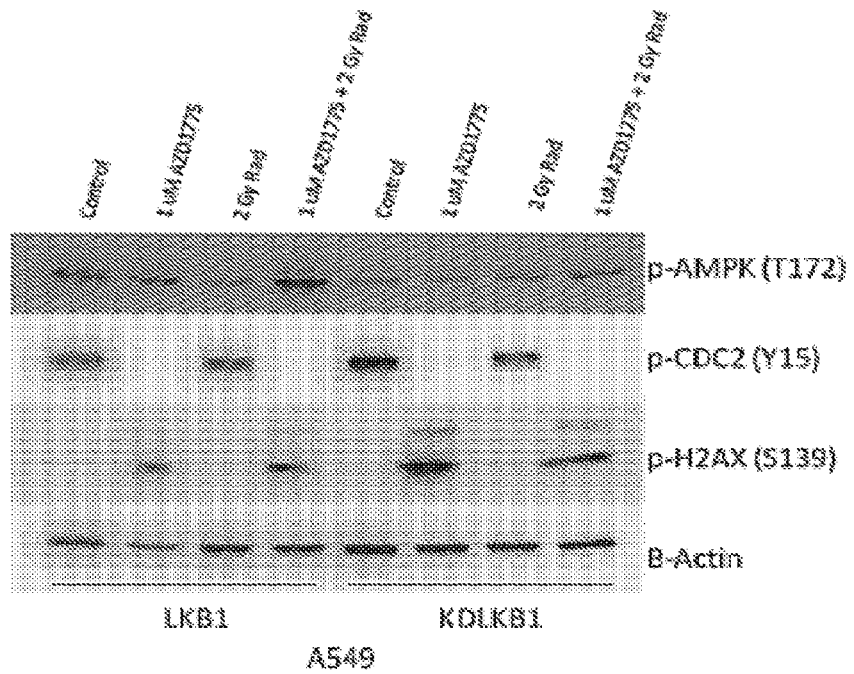
FIG. 4A illustrates, in accordance with embodiments herein, the examination of cell signaling molecules in A549 cells, including both rescue and control conditions. The cells were treated with AZD1775 alone and in combination with 2Gy of ionizing radiation. The LKB1-cells exhibited increased amounts of phosphorylated AMPK, but the LKB1-deficient cells exhibited increased amount of phosphorylated H2AX, which is a known indicator of DNA damage.
Figure 4B:
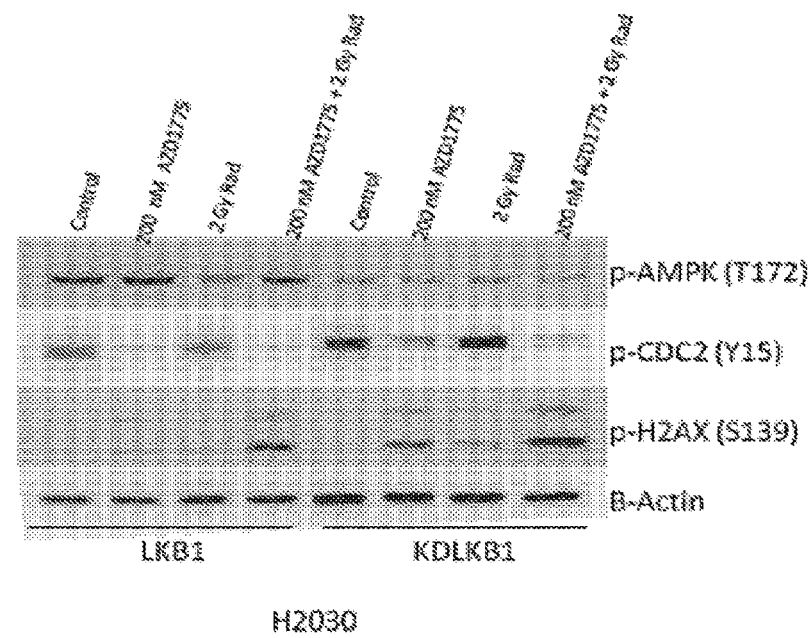
FIG. 4B illustrates, in accordance with embodiments herein, the examination of cell signaling molecules in H2030 cells, including both rescue and control conditions. The cells were treated with AZD1775 alone and in combination with 2Gy of ionizing radiation. The LKB1-cells exhibited increased amounts of phosphorylated AMPK, but the LKB1-deficient cells exhibited increased amount of phosphorylated H2AX, which is a known indicator of DNA damage.

Next, referring now to FIGS. 4A and 4B, the investigators examined cell signaling molecules in A549 and H2030 cells, including both rescue and control conditions. The investigators treated with AZD1775 alone and in combination with 2Gy of ionizing radiation. As illustrated in FIGS. 4A and 4B, the LKB1-cells exhibit increased amounts of phosphorylated AMPK, but the LKB1-deficient cells exhibit increased amount of phosphorylated H2AX, which is a known indicator of DNA damage. As such, this data further illustrates that not only does the combination of AZD1775 and LKB1 deficiency lead to DNA damage and cellular injury, but the addition of a second treatment modality (radiation) can further exacerbate this phenomenon.

Figure 5:
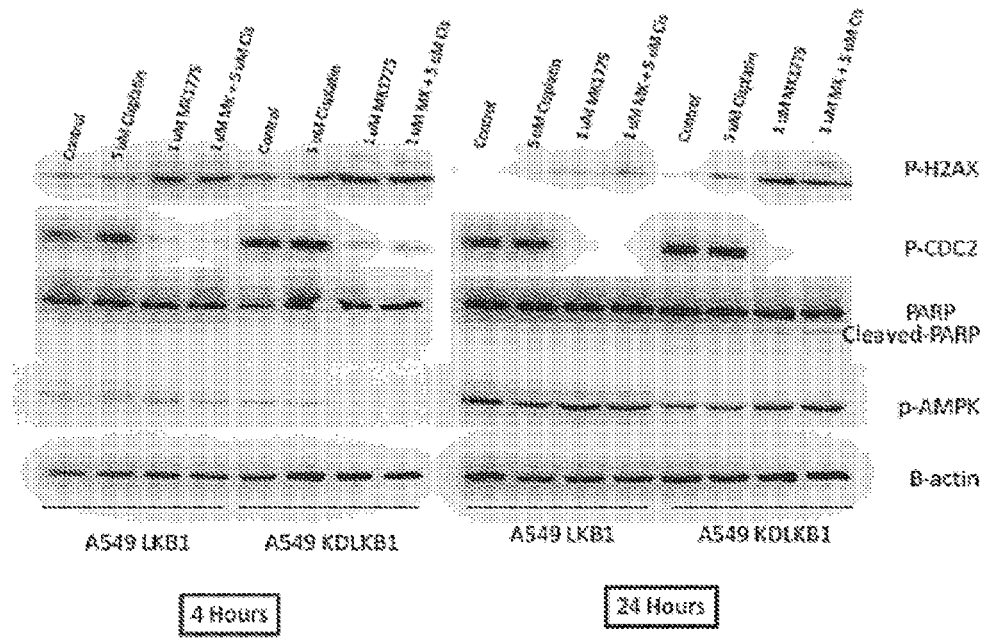
FIG. 5 illustrates, in accordance with embodiments herein, the effect on A549 cells of AZD1775, alone or in combination with another chemotherapeutic (cisplatin) at 4 hours and 24 hours.

Referring now to FIG. 5, the investigators looked at the timing regarding the effects of AZD1775, alone or in combination with another chemotherapeutic (cisplatin). A549 cells (with and without LKB1 rescue transfections) were treated as indicated in FIG. 5 and then total protein was extract 4 hours after treatment and 24 hours after treatment. Significantly, at 24 hours post treatment, there is a discernable increased in the levels of cleaved PARP in the A549 cells that remain LKB1 deficient. This cleaved PARP is an indicator of the induction of apoptosis and efficacy of the combination treatment of AZD1775/MK 1775 and cisplatin.

Figure 6:
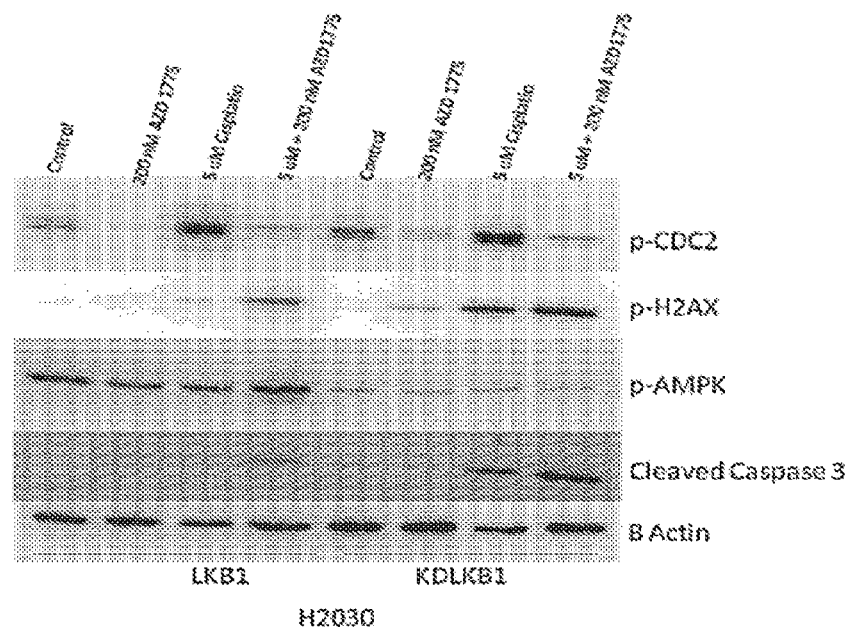
FIG. 6 illustrates, in accordance with embodiments herein, that LKB1 deficient H2030 cells exhibit increased Caspase 3 cleavage when treated with a combination of AZD1775 and cisplatin, with Caspase 3 cleavage being another indicator of the induction of apoptosis.
Figure 7A:
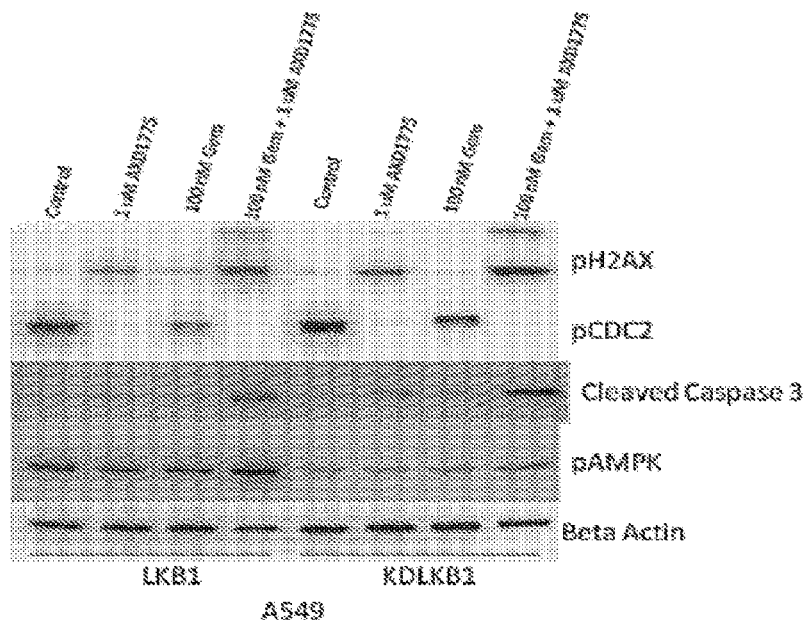
FIG. 7A illustrates, in accordance with embodiments herein, that there is increased detection of cleaved Caspase 3 in A549 cells that are LKB1 deficient and treated with a combination of AZD 175 and gemcitabine.
Figure 7B:
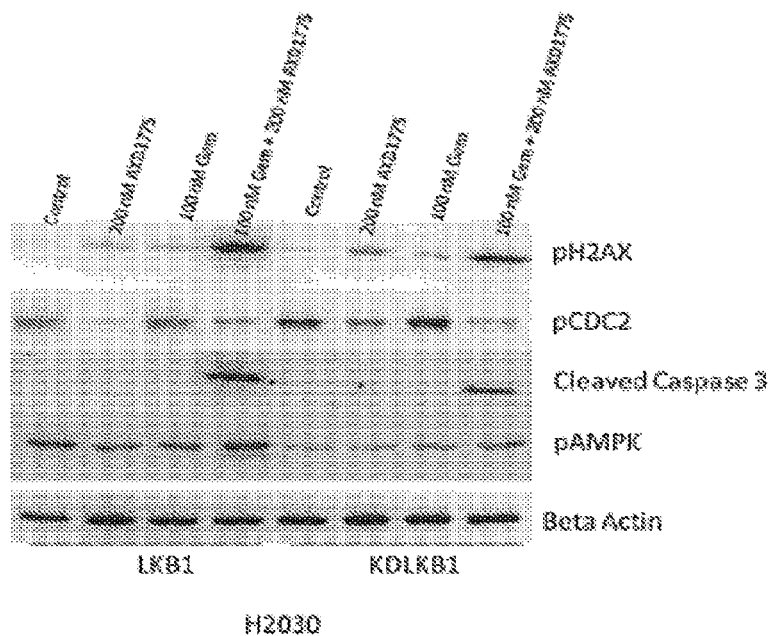
FIG. 7B illustrates, in accordance with embodiments herein, that there is increased detection of cleaved Caspase 3 in H2030 cells that are LKB1 deficient and treated with a combination of AZD175 and gemcitabine.

This is further illustrated in FIG. 6 in which LKB1 deficient H2030 cells exhibit increased Caspase 3 cleavage when treated with a combination of AZD1775 and cisplatin, with Caspase 3 cleavage being another indicator of the induction of apoptosis. A similar phenomenon is also seen in FIGS. 7A and 7B in which there is increased detection of cleaved Caspase 3 in A549 cells that are LKB1 deficient and treated with a combination of AZD175 and gemcitabine (FIG. 7A) and H2030 cells that are LKB1 deficient and treated with the same combination (FIG. 7B).

Figure 8:
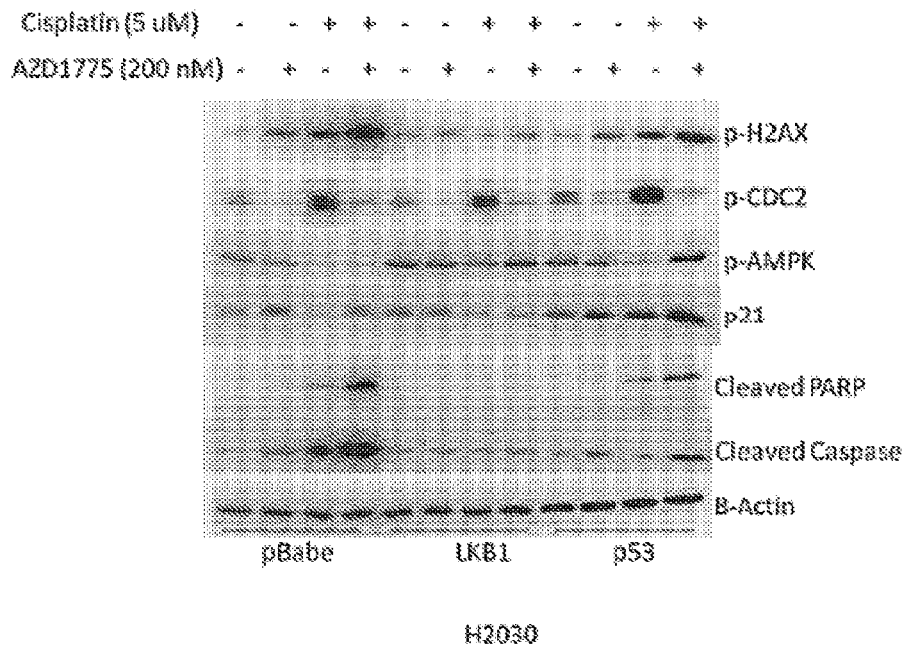
FIG. 8 illustrates, in accordance with embodiments herein, improved treatment capabilities AZD1775 in combination with other chemotherapeutics in LKB1 deficient cells. H2030 cells were divided into three conditions (i) pBabe in which the cells were transfected with an empty vector and remained LKB1 deficient; (ii) LKB1 in which the cells were transfected with a functioning rescue copy of LKB1; and (iii) p53 in which the cells were transfected with a functioning rescue copy of p53 (i.e., the cells functioned as wild type p53 cells). The data in FIG. 8 shows that the combination of AZD1775 and cisplatin leads to significantly increased amounts of cleaved PARP and cleaved Caspase 3, which both indicate an increased amount of apoptosis occurring in this population of H2030 cells. Moreover, cells in the other conditions (LKB1 and p53) did not exhibit the increases in cleaved PARP and Caspase 3, although the p53 cells exhibited increased cleavage of PARP and Caspase 3 relative to the functional LKB1 cells.

Referring to FIG. 8, the investigators further substantiate the improved treatment capabilities AZD1775 in combination with other chemotherapeutics in LKB1 deficient cells. In particular, these H2030 were divided into three conditions (i) pBabe in which the cells were transfected with an empty vector and remained LKB1 deficient; (ii) LKB1 in which the cells were transfected with a functioning rescue copy of LKB1; and (iii) p53 in which the cells were transfected with a functioning rescue copy of p53 (i.e., the cells functioned as wild type p53 cells). The data in FIG. 8 shows that the combination of AZD1775 and cisplatin leads to significantly increased amounts of cleaved PARP and cleaved Caspase 3, which both indicate an increased amount of apoptosis occurring in this population of H2030 cells. Moreover, cells in the other conditions (functioning LKB1 and function p53) did not exhibit the increases in cleaved PARP and Caspase 3, although the p53 cells did exhibit increased cleavage of PARP and Caspase 3 relative to the functional LKB1 cells.

Figure 9:
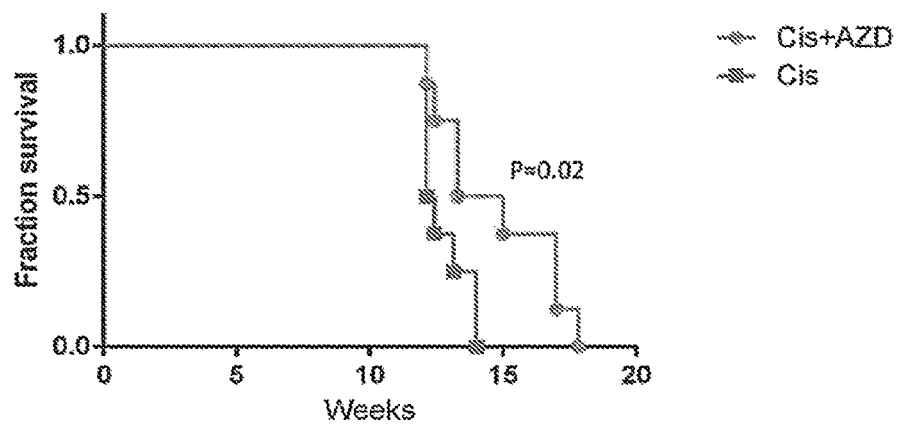
FIG. 9 illustrates, in accordance with embodiments herein, mutant kras/lkb 1 deficient nsclc tumors in transgenic mice. Mice treated with AZD1775+Cisplatin survived longer than mice treated with Cisplatin alone.

Referring to FIG. 9, the investigators transiently infected 6-8 week old $KRas^{G12D}/LKB\ 1^{FL/FL}$/luci with $5 \times 10^6$ P.F.U. of adenoCre via intratracheal inhalation. Mice received scans using the Xenogen IVIS at 8 weeks to identify disease. Mice were then randomized to Cisplatin (once per week, 2.5 mg/kg) or AZD1775 (30 mg/kg, three times per week)+ cisplatin and treated for four weeks. Survival was calculated via log-rank analysis. It was observed that the median survival rate of mice receiving Cisplatin was 12 weeks, whereas the median survival rate of mice receiving Cisplatin+AZD1775 was 14 weeks. For this set of experiments, the hazard ratio was 0.3972, while the confidence interval was 0.0605-0.6086.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A method of treating adenocarcinoma in a subject, the method comprising the steps of (a) identifying at least a portion of adenocarcinoma cells in the subject as deficient in liver kinase B1 (LKB1) and (b) administering a therapeutically effective amount of a Wee1 kinase inhibitor to the subject, wherein the adenocarcinoma in the subject is deficient in liver kinase B1 (LKB1).

2. The method of claim 1, wherein the adenocarcinoma is lung cancer.

3. The method of claim 2, wherein the lung cancer is non-small cell lung cancer.

4. The method of claim 1, wherein the Wee1 kinase inhibitor is AZD1775.

5. The method of claim 1 and further comprising administering a therapeutically effective amount of a second pharmaceutical composition.

6. The method of claim 5, wherein the second pharmaceutical composition comprises at least one of the following: a DNA-damaging compound and a DNA repair-inhibiting compound.

7. The method of claim 5, wherein the second pharmaceutical composition comprises at least one of cisplatin, carboplatin, pemetrexed, gemcitabine, and a combination thereof.

8. The method of claim 1, wherein the adenocarcinoma in the subject has a KRAS mutation.

9. A method of treating lung cancer in a subject, wherein the lung cancer comprises cells that are LKB1 deficient, the method comprising the steps of contacting the LKB1 deficient lung cancer cells with a therapeutically effective amount of a G2/M checkpoint inhibitor, wherein the LKB1 deficiency is indicative of sensitivity to treatment with the G2/M checkpoint inhibitor.

10. The method of claim 9, wherein the lung cancer is non-small cell lung cancer.

11. The method of claim 9, wherein the G2/M checkpoint inhibitor is selected from the group consisting of Wee1 kinase inhibitors, Chk inhibitors, aurora kinase inhibitors, and PLK inhibitors.

12. The method of claim 9, wherein the G2/M checkpoint inhibitor is AZD1775.

13. The method of claim 9, wherein the lung cancer is KRAS mutant.

14. The method of claim 9 and further comprising contacting the lung cancer cells that are LKB1 deficient with a therapeutically effective amount of a second pharmaceutical composition, wherein the therapeutically effective amount of the second pharmaceutical composition is less than an amount that would be used without the G2/M checkpoint inhibitor.

15. A method of treating adenocarcinoma cells in a subject, the method comprising the steps of:
   receiving a sample of the adenocarcinoma cells;
   identifying at least a portion of the sample of the adenocarcinoma cells as sensitive to at least one G2/M checkpoint inhibitor; and
   contacting the adenocarcinoma cells in the subject with a therapeutically effective amount of a G2/M checkpoint inhibitor if the adenocarcinoma cells are determined to be sensitive to one or more G2/M checkpoint inhibitors, wherein sensitivity to the at least one G2/M checkpoint inhibitor is correlated to a deficiency in liver kinase B1 (LKB1).

16. The method of claim 15, wherein the one or more G2/M checkpoint inhibitors is selected from the group consisting of Wee1 kinase inhibitors, Chk inhibitors, aurora kinase inhibitors, and PLK inhibitors.

17. The method of claim 15, wherein the one or more G2/M checkpoint inhibitors is AZD1775.

18. The method of claim 17 and further comprising contacting the adenocarcinoma cells in the subject with a therapeutically effective amount of a second pharmaceutical composition, wherein the therapeutically effective amount of the second pharmaceutical composition is less than an amount that would be used without the AZD1775.

* * * * *